United States Patent
Kim et al.

(10) Patent No.: US 9,650,720 B2
(45) Date of Patent: May 16, 2017

(54) METHOD FOR SURFACE-MODIFYING NEURAL ELECTRODE

(71) Applicant: ELECTRONICS AND TELECOMMUNICATIONS RESEARCH INSTITUTE, Daejeon (KR)

(72) Inventors: Yong Hee Kim, Daejeon (KR); Sang-Don Jung, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 0 days.

(21) Appl. No.: 15/056,948

(22) Filed: Feb. 29, 2016

(65) Prior Publication Data
US 2016/0258070 A1 Sep. 8, 2016

(30) Foreign Application Priority Data
Mar. 4, 2015 (KR) .................. 10-2015-0030383

(51) Int. Cl.
*C23F 1/44* (2006.01)
*C25D 5/48* (2006.01)
(Continued)

(52) U.S. Cl.
CPC ............ *C23F 1/44* (2013.01); *A61B 5/04001* (2013.01); *C23F 1/14* (2013.01); *C23F 1/30* (2013.01);
(Continued)

(58) Field of Classification Search
CPC . A61B 2562/125; A61B 5/04001; C23F 1/44; C23F 1/14; C23F 1/30; C25D 5/48;
(Continued)

(56) References Cited

U.S. PATENT DOCUMENTS

| 8,932,346 B2 * | 1/2015 | Kuehling | A61L 31/08 |
| | | | 623/1.44 |
| 2003/0195601 A1 * | 10/2003 | Hung | A61N 1/0526 |
| | | | 607/116 |

(Continued)

FOREIGN PATENT DOCUMENTS

| KR | 10-2010-0058220 A | 6/2010 |
| KR | 10-1135157 B1 | 4/2012 |
| KR | 10-2012-0067087 A | 6/2012 |

OTHER PUBLICATIONS

Erkin Seker et al., "The fabrication of low-impedance nanoporous gold multiple-electrode arrays for neural electrophysiology studies", Nanotechnology, Mar. 5, 2010, pp. 1-7, vol. 21, 125504, IOP Publishing Ltd.

(Continued)

*Primary Examiner* — Anita Alanko

(57) ABSTRACT

In a method for surface-modifying a neural electrode, a neural electrode array is formed, first and second metal nanoparticles having different solubilities with respect to an etching solution are simultaneously electrode-deposited on a surface of the neural electrode array, and the second metal nanoparticles are selectively etched using the etching solution, thereby forming a porous structure including the first metal nanoparticles on the surface of the neural electrode array.

12 Claims, 5 Drawing Sheets

(51) Int. Cl.
  *C25D 5/10* (2006.01)
  *C25D 3/46* (2006.01)
  *C23F 1/30* (2006.01)
  *C25D 7/00* (2006.01)
  *A61B 5/04* (2006.01)
  *C23F 1/14* (2006.01)
  *C25D 3/48* (2006.01)
  *B82Y 5/00* (2011.01)
  *B82Y 40/00* (2011.01)

(52) U.S. Cl.
  CPC ............... *C25D 3/46* (2013.01); *C25D 3/48* (2013.01); *C25D 5/10* (2013.01); *C25D 5/48* (2013.01); *C25D 7/00* (2013.01); *A61B 2562/125* (2013.01); *B82Y 5/00* (2013.01); *B82Y 40/00* (2013.01)

(58) Field of Classification Search
  CPC ... C25D 5/10; C25D 3/48; C25D 3/46; C25D 7/00; B82Y 40/00; B82Y 5/00
  See application file for complete search history.

(56) References Cited

U.S. PATENT DOCUMENTS

| | | | | |
|---|---|---|---|---|
| 2005/0266040 | A1* | 12/2005 | Gerberding | A61K 31/337 424/423 |
| 2006/0115512 | A1* | 6/2006 | Peacock, III | A61L 31/12 424/422 |
| 2008/0208283 | A1* | 8/2008 | Vetter | A61N 1/0539 607/45 |
| 2010/0127206 | A1 | 5/2010 | Choi et al. | |
| 2013/0066182 | A1* | 3/2013 | Seymour | A61N 1/05 600/377 |
| 2013/0137082 | A1 | 5/2013 | Park et al. | |
| 2014/0020936 | A1* | 1/2014 | Kim | H05K 1/02 174/255 |

OTHER PUBLICATIONS

Yong Hee Kim et al., "In vitro extracellular recording and stimulation performance of nanoporous gold-modified multi-electrode arrays", Journal of Neural Engineering, Nov. 24, 2015, pp. 1-10, vol. 12, 066029, IOP Publishing Ltd.

Benedetto Bozzini et al., "A SERS investigation of the electrodeposition of Ag—Au alloys from free-cyanide solutions", Journal of Electroanalytical Chemistry, 2004, pp. 133-143, vol. 563, Elsevier B.V.

Muhammed K. Gheith et al., "Single-Walled Carbon Nanotube Polyelectrolyte Multilayers and Freestanding Films as a Biocompatible Platform for Neuroprosthetic Implants", Advanced Materials, Sep. 29, 2005, pp. 2663-2670, vol. 17, WILEY-VCH Verlag GmbH & Co. KGaA, Weinheim.

Yi Ding et al., "Nanoporous Gold Leaf: "Ancient Technology"/ Advanced Material", Advanced Materials, Sep. 9, 2004, pp. 1897-1990, vol. 16, No. 21, WILEY-VCH Verlag GmbH & Co. KGaA, Weinheim.

* cited by examiner

−0.9V, 120s 70°C HNO₃ 4m etching

METHOD FOR SURFACE-MODIFYING NEURAL ELECTRODE

CROSS-REFERENCE TO RELATED APPLICATION

The present application claims priority to Korean patent application number 10-2015-0030383 filed on Mar. 4, 2015, the entire disclosure of which is incorporated herein in its entirety by reference.

BACKGROUND

1. Field

An aspect of the present disclosure relates to a method for forming a neural electrode, and more particularly, to a method for surface-modifying a neural electrode.

2. Description of the Related Art

Neural electrodes can be used in in vivo or in vitro neural interface fields. More specifically, the neural electrodes can be used to provide nerves with an electrical stimulus or to measure or record a neural signal.

As materials used for the neural electrodes, a first-generation electrode made of metal wires such as white gold, gold, tungsten and iridium, a second-generation electrode including a semiconductor and a multi-electrode array, a third-generation electrode surface-modified as a nanostructure, and the like are employed. Recently, studies on third-generation electrodes have been actively conducted. Muhammed K. Gheith, Adv. Mater. 2005, 17, 2663-2670 can be referred with respect to materials used for the neural electrodes.

To accurately identify a nervous condition, it is necessary to record neural signals for each nerve cell. To this end, the size of neural electrodes is decreasing to that (about 10 nm) of the nerve cells. However, as the size of the neural electrodes decreased, impedance and thermal noise increase. Therefore, it is difficult to maintain the measurement sensitivity of valid neural signals.

SUMMARY

Embodiments provide a method for surface-modifying a neural electrode, which can improve the performance of the neural electrode by reducing impedance and ensure signal measurement sensitivity of the neural electrode.

According to an aspect of the present disclosure, there is provided a method for surface-modifying a neural electrode, the method including: forming a neural electrode array; simultaneously electrode-depositing, on a surface of the neural electrode array, first and second metal nanoparticles having different solubilities with respect to an etching solution; and selectively etching the second metal nanoparticles using the etching solution, thereby forming a porous structure including the first metal nanoparticles on the surface of the neural electrode array.

The first metal nanoparticle may include a gold nanoparticle, and the second metal nanoparticle may include a silver nanoparticle.

The method may further include combining molecules including a thiol-functional group with the porous structure including the gold nanoparticles.

The first metal nanoparticle may include a platinum nanoparticle, and the second metal nanoparticle may include a gold nanoparticle.

The electrode-depositing may be performed by providing, in an electrolyte solution, the neural electrode array as a working electrode, a counter electrode, and a reference electrode.

A platinum plate may be used as the counter electrode, and an Ag/AgCl electrode in a KCl saturated solution may be used as the reference electrode.

In the electrode-depositing, an alloy of the first and second metal nanoparticles may be formed by applying a voltage ranging from −1.5 V to 1 V to the counter electrode and the working electrode for 0 to 1200 seconds.

The electrolyte solution may be selected as a solution in which the different first and second nanoparticles are simultaneously formed using the electrode-depositing.

The electrolyte solution may include 50 mM $KAu(CN)_2$, 50 mM $K_2Ag(CN)_3$, 0.2 M KCN, and 0.5 M KOH.

The selectively etching of the second metal nanoparticles may include etching the second metal nanoparticles using the etching solution with 25° C. to 90° C. for 0 to 60 minutes.

The etching solution may include a nitric acid ($HNO_3$) solution.

The etching solution may include a KI solution.

BRIEF DESCRIPTION OF THE DRAWINGS

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the example embodiments to those skilled in the art.

In the drawing figures, dimensions may be exaggerated for clarity of illustration. It will be understood that when an element is referred to as being "between" two elements, it can be the only element between the two elements, or one or more intervening elements may also be present. Like reference numerals refer to like elements throughout.

DETAILED DESCRIPTION

Hereinafter, exemplary embodiments of the present disclosure will be described in detail with reference to the accompanying drawings. However, the present disclosure is not limited to the embodiments but may be implemented into different forms. These embodiments are provided only for illustrative purposes and for full understanding of the scope of the present disclosure by those skilled in the art. Further, the scope of the present disclosure should be understood within the scope of the present disclosure defined by the appended claims.

Figure 1:
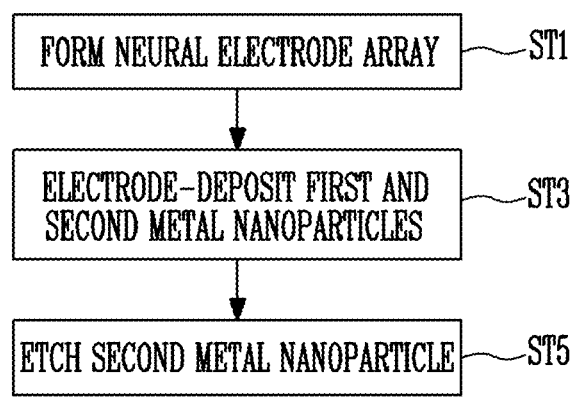
FIG. 1 is a flowchart illustrating a method for surface-modifying a neural electrode according to an embodiment of the present disclosure.

FIG. 1 is a flowchart illustrating a method for surface-modifying a neural electrode according to an embodiment of the present disclosure.

Referring to FIG. 1, a neural electrode array is first formed (ST1). The neural electrode array may be formed by depositing and patterning a metal on a substrate. In this case, the substrate may be a conductive substrate or a flexible substrate. Gold (Au) may be used as a conductive metal for forming the neural electrode array. Patterns constituting the neural electrode array may be micropatterns.

Subsequently, first and second metal nanoparticles different from each other are simultaneously electrode-deposited on a surface of the neural electrode array (ST3). The first and second metal nanoparticles may be formed of materials having different solubilities with respect to a specific etching solution. That is, the first metal nanoparticle may be formed of a material not dissolved by the specific etching solution, and the second metal nanoparticle may be formed of a material dissolved by the specific etching solution. For example, the first metal nanoparticle may be formed of a material not dissolved by a nitric acid ($HNO_3$) solution, and the second metal nanoparticle may be formed of a material dissolved by the nitric acid solution. Alternatively, the first metal nanoparticle may be formed of a material not dissolved by a KI solution, and the second metal nanoparticle may be formed of a material dissolved by the KI solution. More specifically, the first metal nanoparticle may be a gold nanoparticle, and the second metal nanoparticle may be a silver nanoparticle. Alternatively, the first metal nanoparticle may be a platinum nanoparticle, and the second metal nanoparticle may be a gold nanoparticle.

In order to electrode-deposit the different first and second metal nanoparticles on the surface of the neural electrode array, a working electrode having the first and second nanoparticles electrode-deposited thereon is disposed in an electrolyte solution. A counter electrode and a reference electrode are further disposed in the electrolyte solution. A neural electrode array is provided as the working electrode. The counter electrode may be electrically connected to the neural electrode array as the working electrode. A platinum plate may be provided as the counter electrode such that the first metal nanoparticles as the gold nanoparticles and the second metal nanoparticles as the silver nanoparticles are electrode-deposited. An Ag/AgCl electrode in a KCl saturated solution may be provided as the reference electrode such that such that the first metal nanoparticles as the gold nanoparticles and the second metal nanoparticles as the silver nanoparticles are electrode-deposited. A solution capable of simultaneously forming the different first and second metal nanoparticles is selected as the electrolyte solution. For example, the electrolyte solution may include 50 mM $KAu(CN)_2$, 50 mM $K_2Ag(CN)_3$, 0.2 M KCN, and 0.5 M KOH such that the first metal nanoparticles as the gold nanoparticles and the second metal nanoparticles as the silver nanoparticles are electrode-deposited. In order to electrode-deposit the first metal nanoparticles as the gold nanoparticles and the second metal nanoparticles as the silver nanoparticles on the surface of the neural electrode array, a voltage ranging from −1.5 V to 1 V may be applied to the reference electrode and the working electrode for 0 to 1200 seconds. More specifically, a voltage of 0.9 V may be applied to the reference electrode and the working electrode for 120 seconds. Accordingly, the first and second metal nanoparticles can be electrode-deposited on the surface of the neural electrode array by being moved to a surface of the working electrode by current flowing between the working electrode and the counter electrode. The reference electrode may control the flow of the current between the working electrode and the counter electrode to be fast. In the above-described electrode-depositing, an alloy of the first and second metal nanoparticles may be deposited on the surface of the neural electrode array.

Subsequently, the second metal nanoparticles among the first and second metal nanoparticles electrode-deposited on the surface of the neural electrode array using an electrode-deposition technique are selectively etched using an etching solution (ST5). Accordingly, a porous structure including the first metal nanoparticles can be formed on the surface of the neural electrode array. That is, the neural electrode array can have a surface modified with nanoporous structures. The selective etching of the second metal nanoparticles may be performed using an etching solution with normal temperature (25° C.) to 90° C. for 0 to 60 minutes. More specifically, the selective etching of the second metal nanoparticles may be performed in an etching solution with 70° C. for four minutes.

As an example, when gold and silver nanoparticles are electrode-deposited on a surface of a neural gold electrode array, only the silver nanoparticles are selectively etched. The selective etching of the silver nanoparticles may be performed using a nitric acid ($HNO_3$) solution with 25° C. to 90° C. for 0 to 60 minutes. Accordingly, the neural gold electrode array has a surface including porous gold nanoparticles.

As another example, when platinum and gold nanoparticles are electrode-deposited on a surface of a neural electrode array, only the gold nanoparticles are selectively etched. The selective etching of the silver nanoparticles may be performed using a KI solution with 25° C. to 90° C. for 0 to 60 minutes. Accordingly, the neural electrode array has a surface including porous platinum nanoparticles.

If the surface of the neural electrode array is modified with porous metal nanoparticles as described above, the surface area of a neural electrode per unit area increases, and thus the impedance of the neural electrode can be reduced. As the impedance of the neural electrode is lowered, electrical noise can be reduced. Accordingly, the neural electrode array according to the embodiment of the present disclosure has a surface modified with porous metal nanoparticles, thereby improving a signal-to-noise ratio.

In the embodiment of the present disclosure, a neural electrode having a surface modified with porous metal nanoparticles can be provided not using a vacuum apparatus such as a sputter having a high installation cost but using a relatively simple method including electrode-deposition and wet etching processes.

If the surface of the neural electrode array is modified with porous gold nanoparticles, the biocompatibility and surface-modification performance of the neural electrode can be improved. This is because gold has not only excellent biocompatibility but also excellent reactivity with a thiol-functional group easily combined with another material.

Although not shown in this figure, the method according to the embodiment of the present may further include combining molecules including a thiol-functional group with the surface of the neural electrode array, modified with the porous gold nanoparticles. Since the gold nanoparticle has high reactivity with the thiol-functional group, the molecules including the thiol-functional group can be stably chemically combined with the surface of the neural electrode array including the porous gold nanoparticles. The thiol-functional group combined with the porous gold nanoparticle may be combined with biomaterials. Accordingly, the thiol-functional group combined with various biomaterials can perform surface processing on the surface of the neural electrode array. The thiol-functional group provides a stable combination between nerve cells and the neural electrode array, thereby enhancing the measurement ability of neural signals.

Figure 2A:
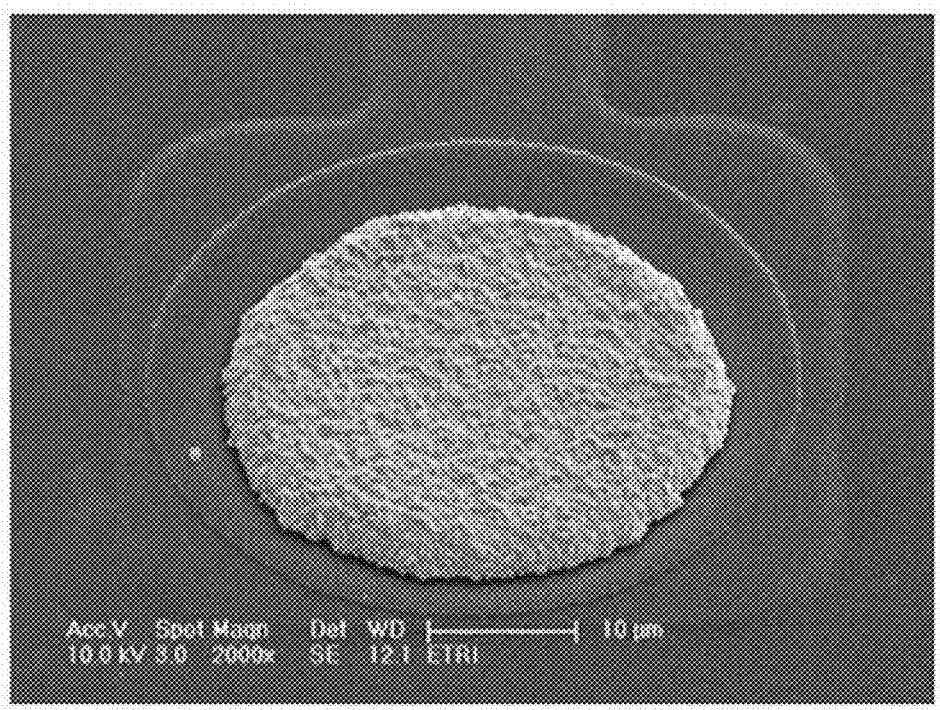
FIG. 2A is a view showing a sample obtained by coating a surface of a neural gold electrode array with an alloy of gold and silver nanoparticles using an electrode-deposition technique according to an embodiment of the present disclosure.
Figure 2B:
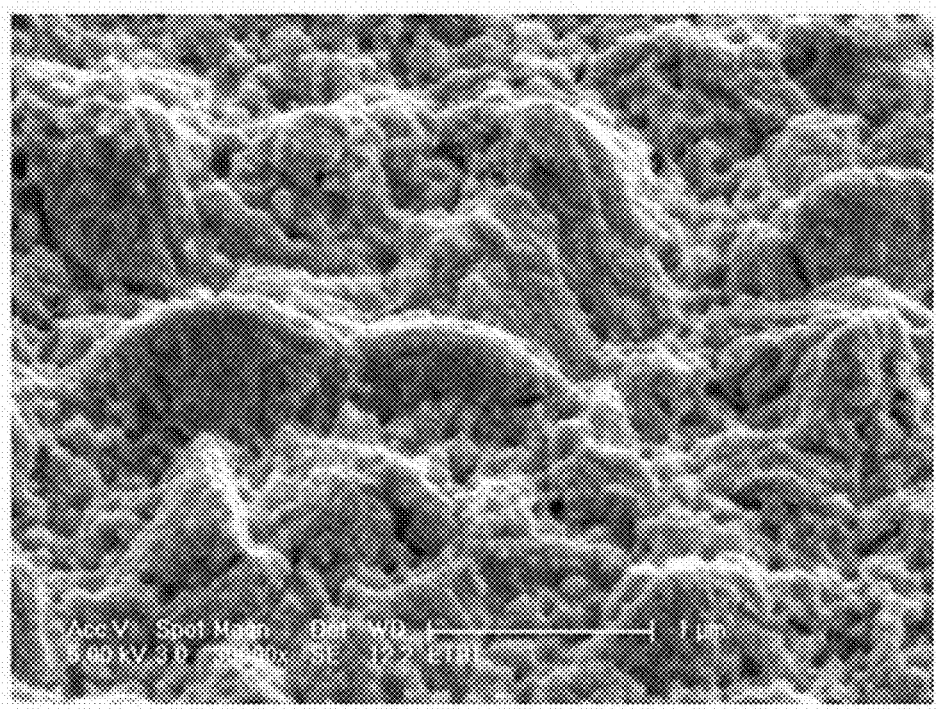
FIG. 2B is a enlarged scanning electron microscope (SEM) photograph of the sample of FIG. 2A.

FIG. 2A is a view showing a sample obtained by coating a surface of a neural gold electrode array with an alloy of gold and silver nanoparticles using an electrode-deposition technique according to an embodiment of the present disclosure. FIG. 2B is a enlarged scanning electron microscope (SEM) photograph of the sample of FIG. 2A.

Figure 3:
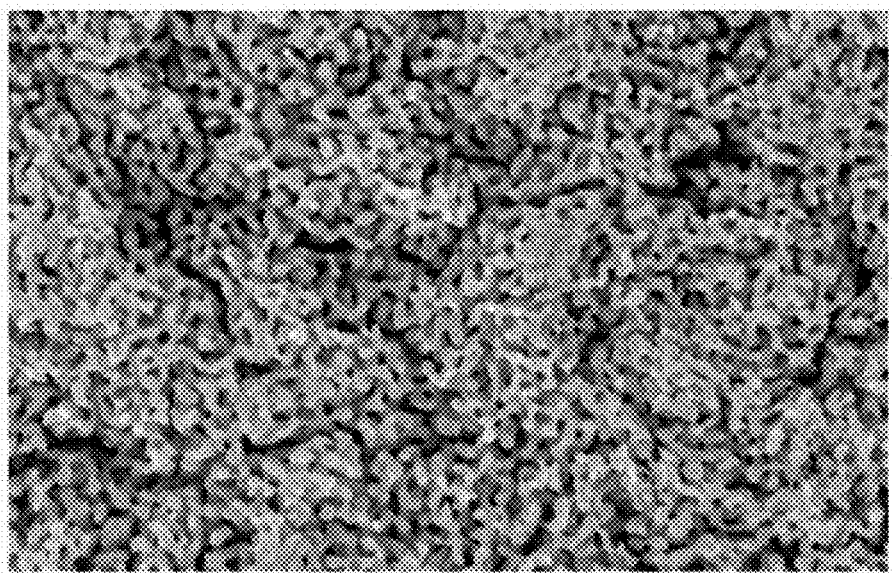
FIG. 3 is an SEM photograph showing a surface of the sample of FIG. 2A after the silver nanoparticles of the sample are selectively etched using a nitric acid solution.

FIG. 3 is an SEM photograph showing a surface of the sample of FIG. 2A after the silver nanoparticles of the sample are selectively etched using a nitric acid solution.

Referring to FIGS. 2A, 2B and 3, it can be seen that the surface of the neural electrode array is modified to have porosity after the silver nanoparticles are selectively etched.

Figure 4A:
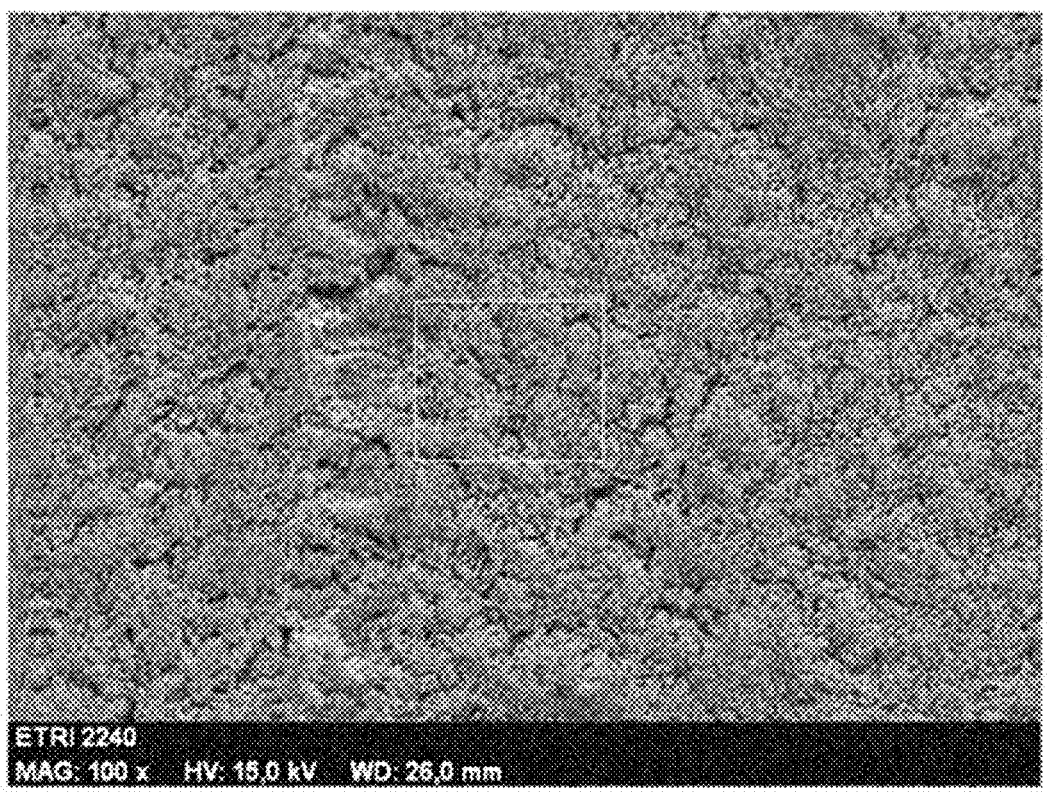
FIG. 4A is a view showing the sample of FIG. 2A after the silver nanoparticle of the sample are selectively etched.
Figure 4B:
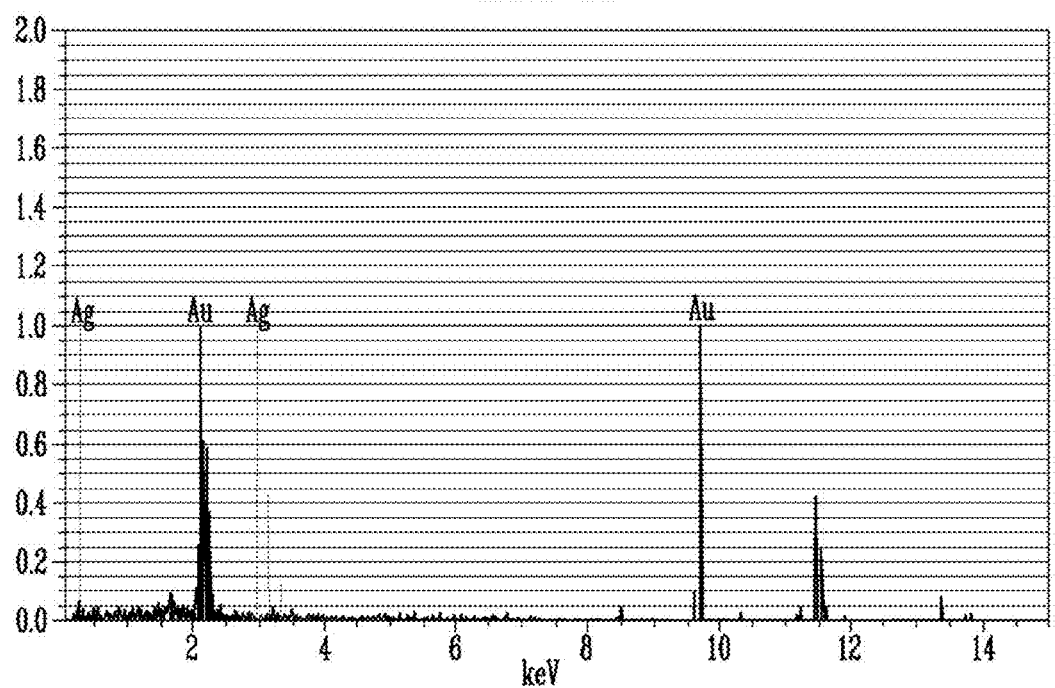
FIG. 4B is a view showing a result obtained by performing energy dispersive X-ray spectroscopy (EDX) analysis on the sample of FIG. 4A.

FIG. 4A is a view showing the sample of FIG. 2A after the silver nanoparticle of the sample are selectively etched. FIG. 4B is a view showing a result obtained by performing energy dispersive X-ray spectroscopy (EDX) analysis on the sample of FIG. 4A. Referring to FIG. 4B, silver (Ag) is barely detected.

Figure 5:
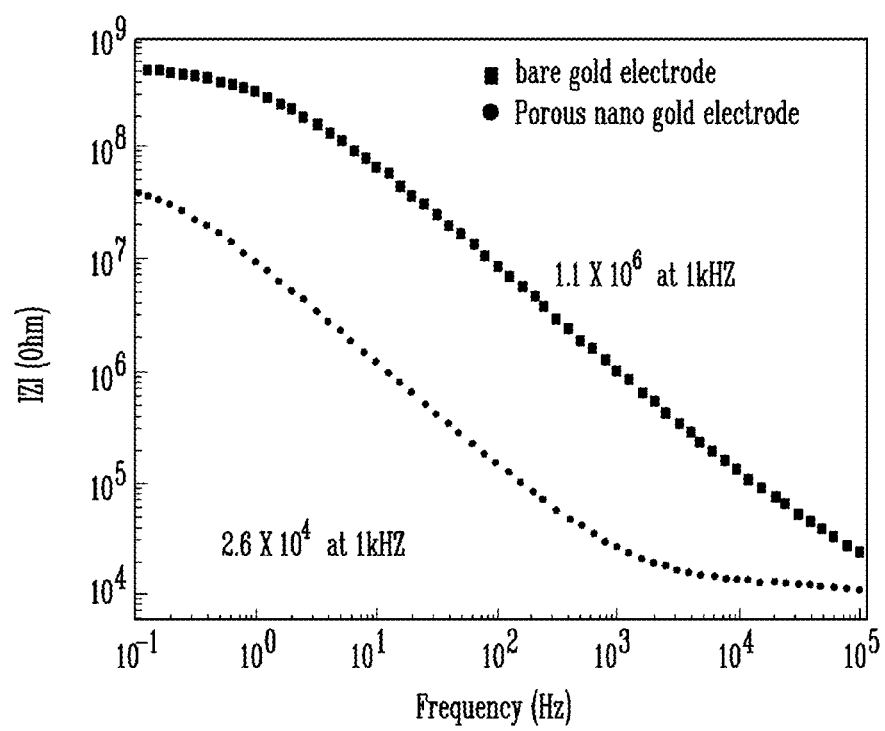
FIG. 5 is a graph comparing impedances of a bare gold electrode and a porous nano gold electrode.

FIG. 5 is a graph comparing impedances of a bare gold electrode and a porous nano gold electrode.

Referring to FIG. 5, it can be seen that the impedance of the porous nano gold electrode is lower than that of the bare gold electrode.

According to the present disclosure, different metal nanoparticles are electrode-deposited on the surface of the neural electrode array, and any one of the different metal nanoparticles is selectively etched, so that the surface of the neural electrode array can be modified to have porosity.

Also, if the surface of the neural electrode array is modified to have porosity, the surface area of the neural electrode array per unit area increases. Thus, thermal noise can be reduced by reducing impedance, and the measurement sensitivity of valid neural signals can be ensured.

Also, metal nanoparticles etched by a specific etching solution and metal nanoparticles not etched by the specific etching solution are simultaneously coated on the surface of the neural electrode array using the electrode-deposition technique, thereby reducing cost required to coat the metal nanoparticles.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present disclosure as set forth in the following claims.

What is claimed is:

1. A method for surface-modifying a neural electrode, the method comprising:
    forming a neural electrode array;
    simultaneously electrode-depositing, on a surface of the neural electrode array, first and second metal nanoparticles having different solubilities with respect to an etching solution; and
    selectively etching the second metal nanoparticles using the etching solution, thereby forming a porous structure including the first metal nanoparticles on the surface of the neural electrode array.

2. The method of claim 1, wherein the first metal nanoparticle includes a gold nanoparticle, and the second metal nanoparticle includes a silver nanoparticle.

3. The method of claim 2, further comprising combining molecules including a thiol-functional group with the porous structure including the gold nanoparticles.

4. The method of claim 1, wherein the first metal nanoparticle includes a platinum nanoparticle, and the second metal nanoparticle includes a gold nanoparticle.

5. The method of claim 1, wherein the electrode-depositing is performed by providing, in an electrolyte solution, the neural electrode array as a working electrode, a counter electrode, and a reference electrode.

6. The method of claim 5, wherein a platinum plate is used as the counter electrode, and an Ag/AgCl electrode in a KCl saturated solution is used as the reference electrode.

7. The method of claim 5, wherein, in the electrode-depositing, an alloy of the first and second metal nanoparticles is formed by applying a voltage ranging from −1.5 V to 1 V to the counter electrode and the working electrode for 0 to 1200 seconds.

8. The method of claim 5, wherein the electrolyte solution is selected as a solution in which the different first and second nanoparticles are simultaneously formed using the electrode-depositing.

9. The method of claim 8, wherein the electrolyte solution includes 50 mM $KAu(CN)_2$, 50 mM $K_2Ag(CN)_3$, 0.2 M KCN, and 0.5 M KOH.

10. The method of claim 1, wherein the selectively etching of the second metal nanoparticles includes etching the second metal nanoparticles using the etching solution with 25° C. to 90° C. for 0 to 60 minutes.

11. The method of claim 10, wherein the etching solution includes a nitric acid ($HNO_3$) solution.

12. The method of claim 10, wherein the etching solution includes a KI solution.

* * * * *